(12) United States Patent
Herrmann

(10) Patent No.: US 6,878,106 B1
(45) Date of Patent: Apr. 12, 2005

(54) DEFORMABLE FIBERSCOPE WITH A DISPLACEABLE SUPPLEMENTARY DEVICE

(76) Inventor: Ingo F. Herrmann, Voltzweg 5, Munich (DE), D-81479

( * ) Notice: Subject to any disclaimer, the term of this patent is extended or adjusted under 35 U.S.C. 154(b) by 298 days.

(21) Appl. No.: 09/913,617

(22) PCT Filed: Aug. 24, 2000

(86) PCT No.: PCT/EP00/01200
§ 371 (c)(1),
(2), (4) Date: Jan. 8, 2002

(87) PCT Pub. No.: WO00/48506
PCT Pub. Date: Aug. 24, 2000

(30) Foreign Application Priority Data

Feb. 15, 1999 (DE) .......................................... 199 06 191

(51) Int. Cl.$^7$ ............................................. A61B 1/018
(52) U.S. Cl. ........................ 600/104; 600/106; 600/128
(58) Field of Search ............................... 600/106, 128, 600/104, 153, 127, 129

(56) References Cited

U.S. PATENT DOCUMENTS

| | | |
|---|---|---|
| 1,891,054 A | 12/1932 | Pitman |
| 3,858,577 A | 1/1975 | Bass et al. |
| 5,025,778 A * | 6/1991 | Silverstein et al. ......... 600/104 |
| 5,154,164 A | 10/1992 | Chikama |
| 5,217,001 A * | 6/1993 | Nakao et al. ............... 600/123 |
| 5,259,366 A * | 11/1993 | Reydel et al. .............. 600/124 |
| 5,503,616 A * | 4/1996 | Jones ......................... 600/153 |
| 5,509,892 A * | 4/1996 | Bonnet ....................... 600/156 |
| 5,643,175 A * | 7/1997 | Adair ......................... 600/153 |
| 5,685,822 A * | 11/1997 | Harhen ...................... 600/129 |
| 5,749,889 A * | 5/1998 | Bacich et al. ............... 600/153 |
| 5,891,013 A * | 4/1999 | Thompson .................. 600/104 |
| 5,904,648 A | 5/1999 | Arndt et al. |
| 6,059,719 A * | 5/2000 | Yamamoto et al. ......... 600/127 |
| 6,071,233 A * | 6/2000 | Ishikawa et al. ............ 600/104 |

FOREIGN PATENT DOCUMENTS

| | | |
|---|---|---|
| DE | 9004534.3 | 11/1990 |
| DE | 9208381.1 | 12/1993 |
| WO | WO 9741767 A2 | 11/1997 |
| WO | WO 99/27840 A1 | 6/1999 |

OTHER PUBLICATIONS

S. Arce Recio, et al. "Functional pharyngoesophagoscopy: a new technique for analyzing deglutition" *Surgery and Prosthelic Voice Restoration after Total and Subtotal Laryngectomy*, 1996, pp. 243–251.

* cited by examiner

Primary Examiner—John P. Leubecker
(74) Attorney, Agent, or Firm—Townsend and Townsend and Crew LLP

(57) ABSTRACT

The invention relates to a deformable endoscope that has one or more light/image transmission passages and in which at least one additional instrument is provided, wherein the unit of endoscope and additional instrument has a non-round cross-section along a longitudinal section (insertion section) to be inserted into a human or animal body orifice. The light/image transmission passage or the plurality of light/image transmission passages form—in particular together with at least one work passage—a closed unit (fiberscope part) which can be separated from the additional instrument. The fiberscope part and the additional instrument can be displaced relatively relative to one another along their longitudinal directions. A holding unit is provided for the holding and/or guiding of the fiberscope part and the additional instrument relative to one another.

22 Claims, 8 Drawing Sheets

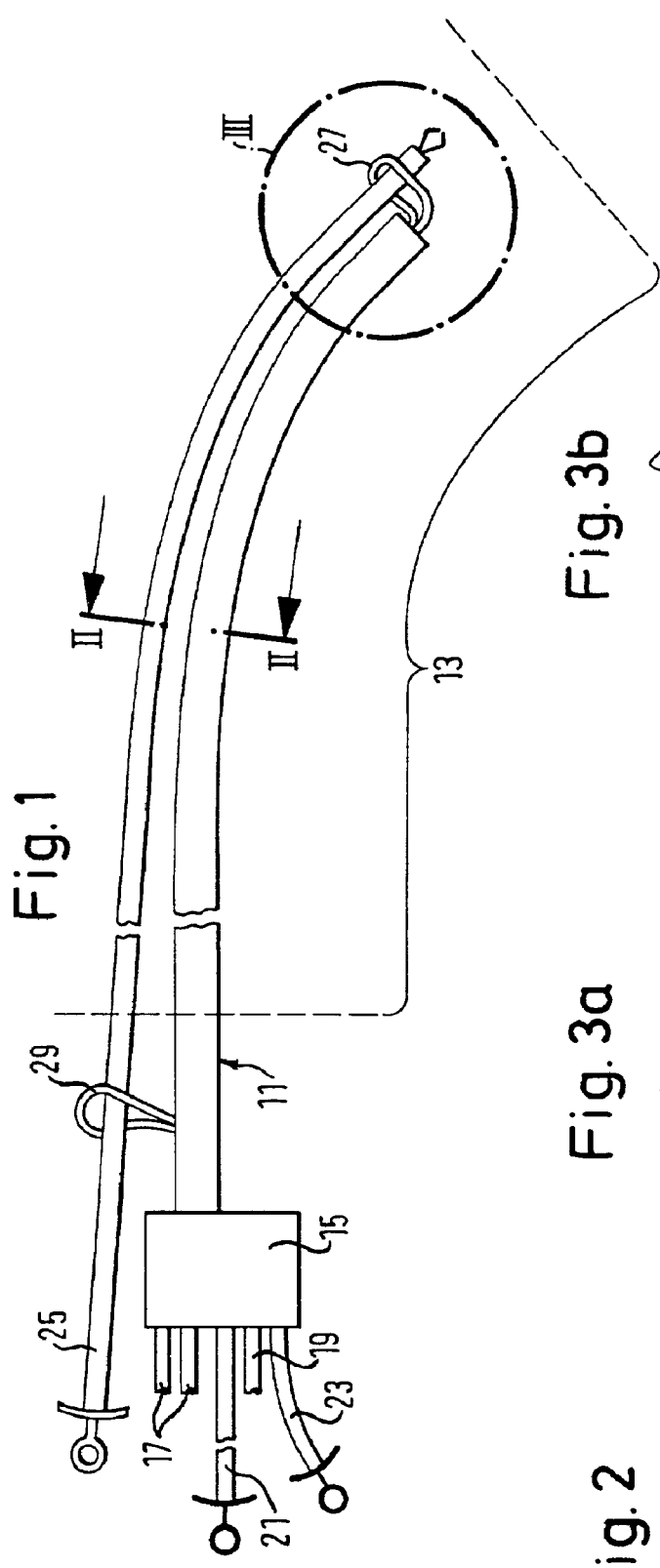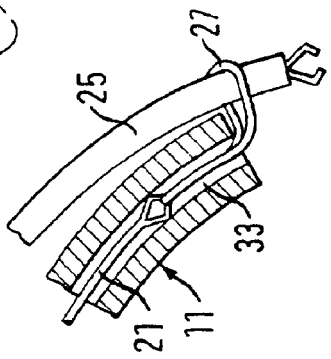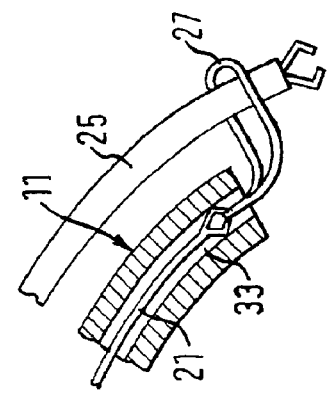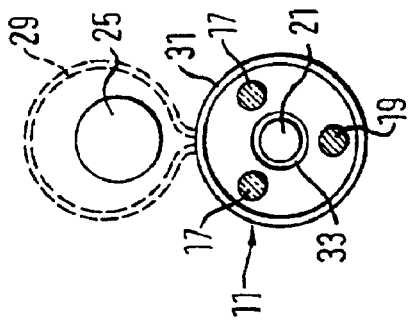

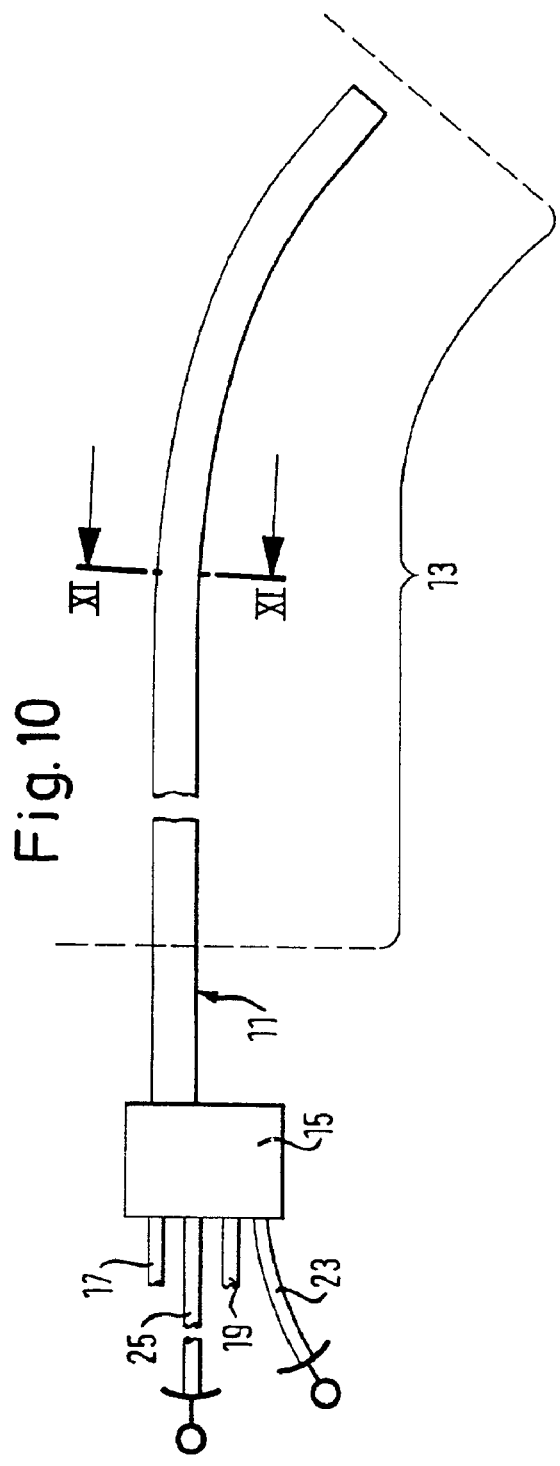
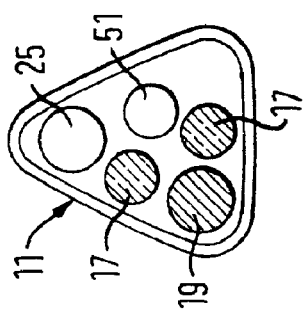
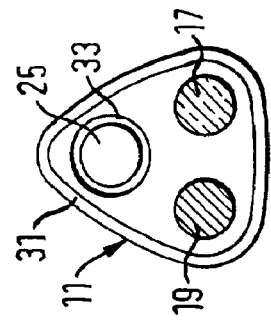

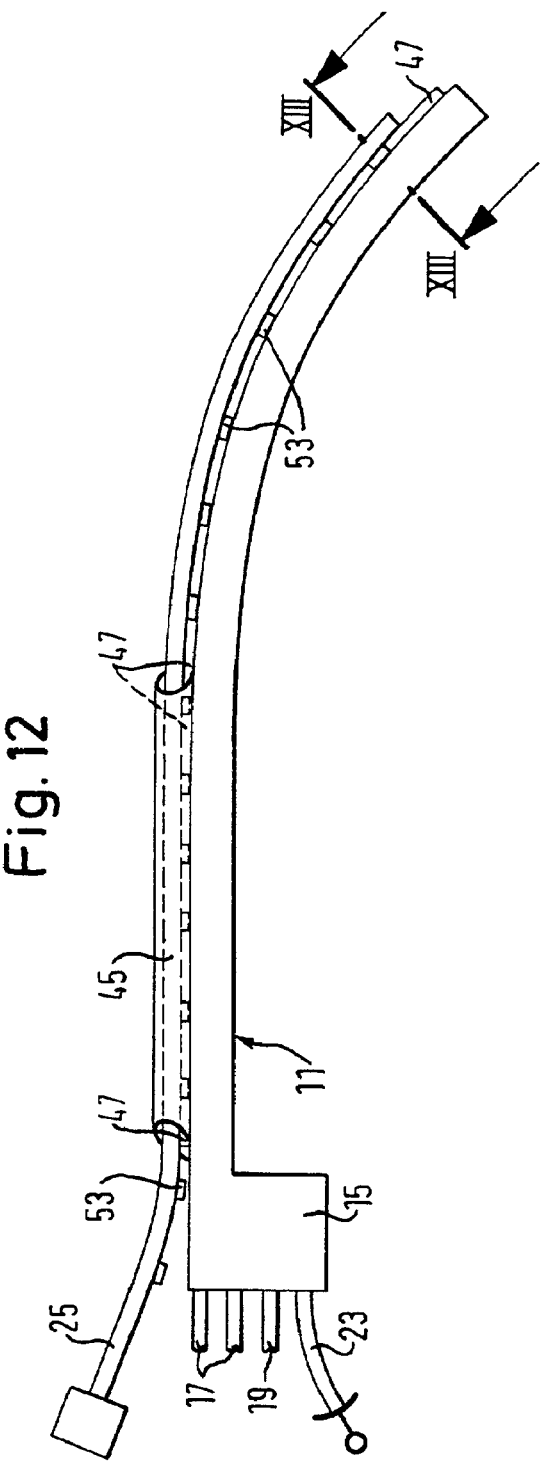
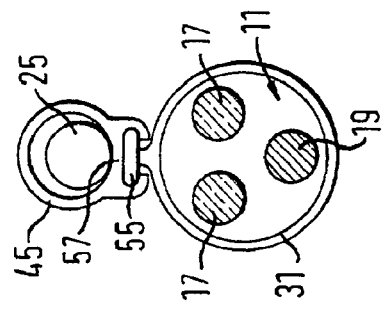
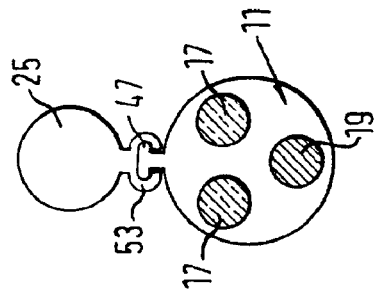

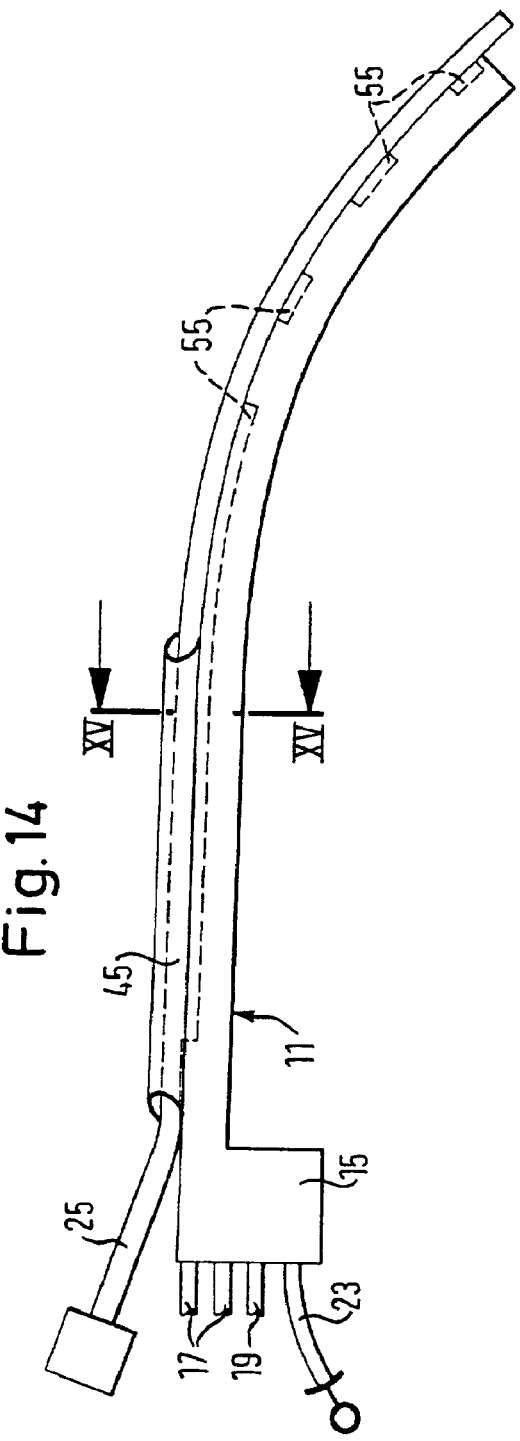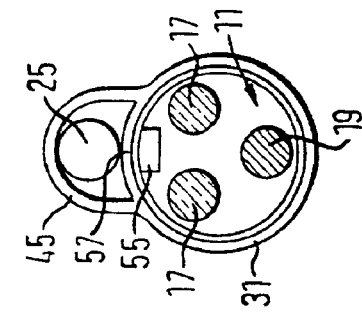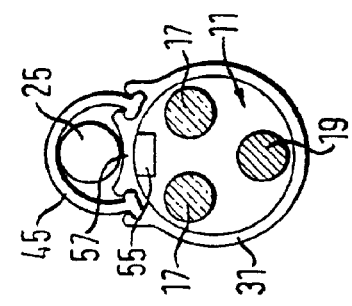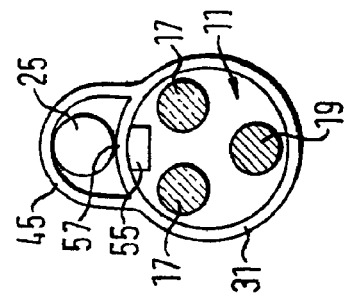

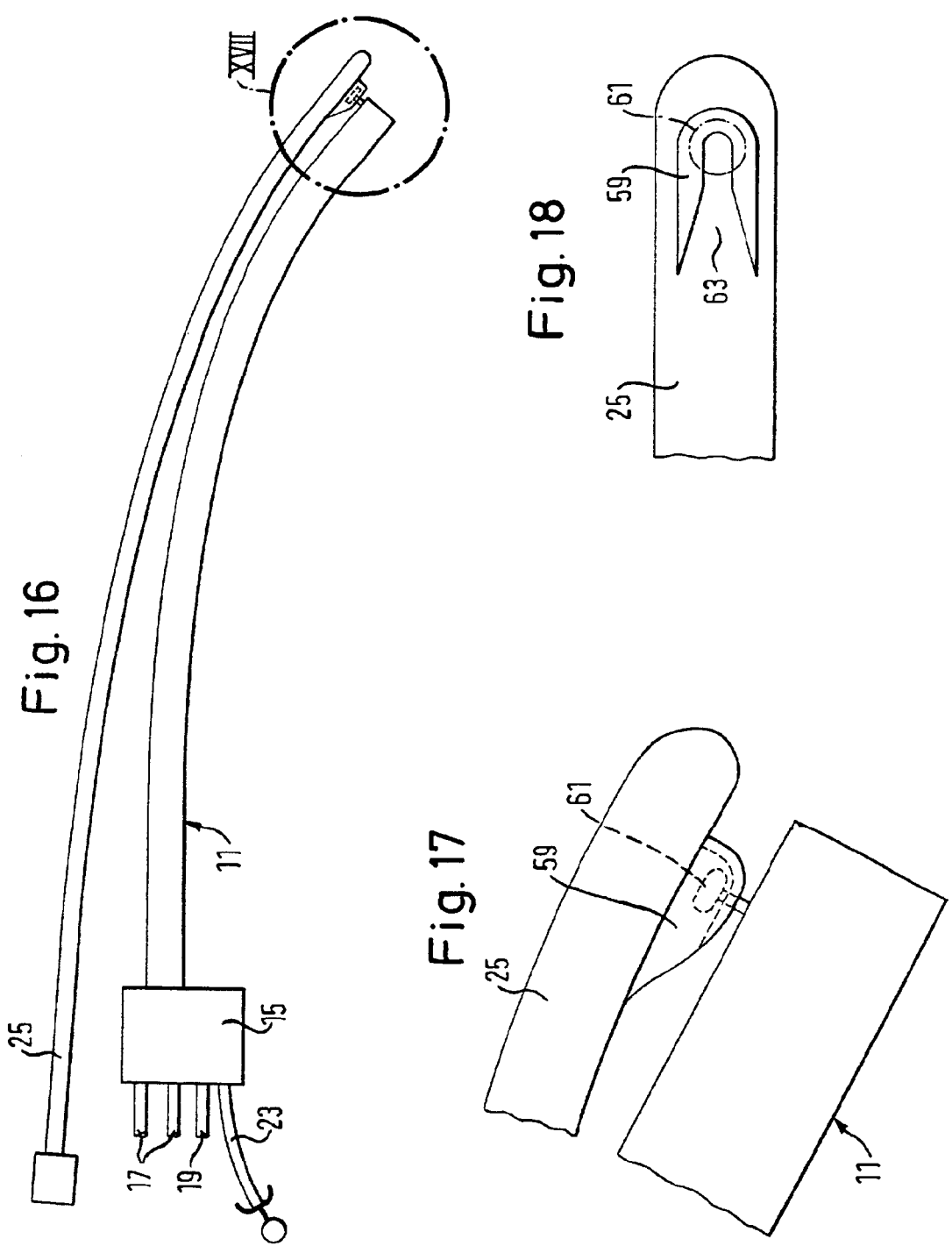

DEFORMABLE FIBERSCOPE WITH A DISPLACEABLE SUPPLEMENTARY DEVICE

BACKGROUND OF THE INVENTION

The invention relates to a deformable endoscope that has one or more light/image transmission passages and in which at least one additional instrument is provided.

Gastroscopes are known, for example, which are inserted via the patient's mouth into the esophagus and stomach for a gastroscopy. Such gastroscopes have a central work passage into which small biopsy forceps, for example, can be inserted as an additional instrument in order to take a tissue sample from the stomach or esophagus under observation via the light/image transmission passage.

Disadvantages of these known endoscopes can be that their application possibilities are limited to an unwanted extent and that their use is a strain on the patient. In particular, a prior sedation medication is required for the insertion of known endoscopes. An unintended injury to the patient, for example to the pharyngeal mucosa, by an orally inserted gastroscope cannot always be avoided.

SUMMARY OF THE INVENTION

It is an object of the invention to provide an endoscope that offers a wider range of applications than known endoscopes with a lower risk of injury and a more pleasant subjective perception by the patient.

This object is satisfied for an endoscope of the kind first mentioned by the unit of endoscope and additional instrument having a non-round cross-section along a longitudinal section (insertion section) to be inserted into a human or animal body orifice; by, furthermore, the light/image transmission passage or the plurality of light/image transmission passages forming—in particular together with at least one work passage—a closed unit (fiberscope) which can be separated from the additional instrument; by, furthermore, the fiberscope part and the additional instrument being displaceable relative to one another along their longitudinal directions; and by a holder device being provided for the holding and/or guiding of the fiberscope part and the additional instrument relative to one another.

The invention thus departs from the long-held traditional view that endoscopes have to be provided with an essentially circular cross-section. The cross-section of the insertion section of the endoscope in accordance with the invention is not rotationally symmetrical, so that the endoscope can be better matched to the intended applications.

The cross-section of the insertion section is preferably matched to the cross-section of the body orifice into which the endoscope should be inserted and which generally does not have a round cross-section. The utilization of space can thereby be optimized, in particular at the narrowest point of the body for the insertion of the endoscope. This results in a more pleasant subjective perception by the patient and there can be more space available in the patient's body for the desired diagnostic or therapeutic measure. A particular advantage of such a matching to the cross-section lies in the fact that a sedation medication, relaxation agent or anesthization can be omitted in many applications since defense reflexes of the patients can be avoided more easily due to the optimized utilization of the cross-section and the space.

Since the cross-section of the endoscope does not have a round shape, an advantageous stability of the inserted endoscope can furthermore be achieved with respect to unwanted twisting with respect to its longitudinal direction. An unwanted twisting of the endoscope can result in the course of the insertion procedure with the round cross-section of known endoscopes. If, however, the endoscope is—as is provided by the invention—formed asymmetrically in cross-section, the shape of the body orifice into which the endoscope is inserted can be utilized to block a twisting of the inserted endoscope. This facilitates the further insertion of the endoscope and reduces the risk of injury.

The design of the endoscope of the invention can be realized by the additional instrument being arranged—contrary to the design of known endoscopes—at a non-central position within the cross-section of the insertion section. In particular, a work passage provided for the reception of the additional instrument can be provided not at a central position, but in a lateral, eccentric arrangement with respect to the longitudinal access of the endoscope.

The embodiment of the endoscope of the invention can also be achieved by the dimension of the cross-section of its insertion section being much larger in one direction than the dimension in a direction orthogonal thereto, for example by a factor of at least 1.5. The cross-section can, for example, correspond approximately to an isosceles triangle or a mirror-symmetrical trapezium whose corners are rounded in each case.

In a preferred embodiment, the endoscope is formed as a pharingo-esophago-gastroscope for the examination of the pharynx, the esophagus or the stomach of the patient, by the cross-section of the insertion section of the whole endoscope being matched to the cross-section of a meatus of the nose. Such an endoscope can—in contrast to conventional gastroscopy—be inserted into the pharynx and the esophagus of the patient via a meatus of the nose.

The pharingo-esophago-gastroscope of the invention offers the following advantages, among others:

a) in the nasal insertion into the pharynx and into the esophagus, an injury to the patient, in particular to the pharyngeal mucosa, can be avoided particularly easily due to the simultaneous optical monitoring via the light/image transmission passage and due to the deformability of the pharingo-esophago-gastroscope;

b) in contrast to the oral insertion of a known gastroscope, the nasal insertion of the endoscope of the invention does not produce any defense reflexes, in particular no biting reflexes, in the patient;

c) in contrast to conventional gastroscopy, no local sedation medication of the larynx region is required, so that the patient is not affected in this respect by the use of the endoscope of the invention and can leave the doctor's surgery or the clinic without problems after the application without having to wait for a sedation measure to wear off;

d) when the pharingo-esophago-gastroscope of the invention is used, there are also lower personnel requirements since the assistance of a nurse and a helper (second nurse) can be dispensed with and no anesthetist is required either. The use of the pharingo-esophago-gastroscope can be carried out by one single doctor with his practice assistant. A specifically fitted endoscopy room (operating theater) is not necessary. The use of the pharingo-esophago-gastroscope instead takes place in a normal examination chair in the doctor's office. This naturally considerably reduces the application costs;

e) due to the optimized cross-section of the pharingo-esophago-gastroscope of the invention and its thus comparatively small cross-sectional area, it is perceived by the patient as more pleasant than a conventional gastroscope which usually has a circular cross-section of approximately 11 mm and thereby takes up unnecessary extra room. A contribution to this more pleasant perception is also made by the fact that the pharingo-esophago-gastroscope is inserted nasally so that the comparatively sensitive mouth area remains free of foreign bodies;

f) the pharingo-esophago-gastroscope inserted through a single meatus of the nose allows the patient to continue to breathe both through the mouth and through the nose, namely through the non-occupied meatus of the nose;

g) the pharingo-esophago-gastroscope inserted nasally into the pharyngeal cavity can be further guided into the esophagus in a particularly simple, pleasant and non-hazardous manner when the patient simultaneously drinks a liquid, for example water. This is possible without problem due to the free mouth area. The drinking process can be tracked by the physician via the light/image transmission passage. When swallowing takes place, the pharingo-esophago-gastroscope is guided past the larynx and the esophagus sphincter into the esophagus;

h) the nasally inserted endoscope allows a study which is close to reality of the swallowing motor system, the contraction movements of the esophagus muscles (peristole) and the associated sphincter. These examinations can take place while using the additional instrument and with simultaneous monitoring via the light/image transmission passage. Such functional analyses can take place both when drinking a liquid and when ingesting solid food. More accurate examination results are found than with known gastroscopes since the mouth area is not blocked by the nasally inserted pharingo-esophago-gastroscope and since the pharingo-esophago-gastroscope has a lower, and thus less disturbing, cross-sectional area due to its optimized cross-section;

i) the use of the endoscope of the invention is not limited to diagnostic procedures, but also opens up new possibilities to study the human or animal body. For example, the pharingo-esophago-gastroscope matched to the meatus of the nose allows the exploration of the new area of study of so-called somnoscopy:

Since the nasally inserted endoscope continues to give the patient the opportunity to breathe through the mouth or nose and since it is also not felt to be particularly unpleasant by the patient, the endoscope can be left in the patient's body overnight without problem in order to carry out studies taking several hours. For example, a pH measuring probe can be used as the additional instrument of the endoscope of the invention and can determine the pH overnight at a plurality of points along the esophagus and in the stomach in order to check whether unexpected local or temporal anomalies occur in comparatively undisturbed and stationary conditions. Of course, the possibility of an optical control via the light/image passage is maintained with such an application.

When the endoscope is formed as a pharingo-esophago-gastroscope, it is preferred if the base length of the basic form of the cross-section, that is, for example, the explained triangular or trapezoidal shape, amounts to a maximum of 3.5 mm. Exhaustive studies have shown that with such a dimension, the insertion of the endoscope into a meatus of the nose is still basically possible with all patients. It is moreover preferred if the maximum cross-section of the respective additional instruments amounts to at most approximately 3 mm, in particular a maximum of approximately 2 mm so that the additional instrument can be guided, together with the remaining pharingo-esophago-gastroscope, through a meatus of the nose of any patient without problem. The cross-section of the additional instrument can, however, also be matched to the individual maximum cross-section of the patient's meatus of the nose. The typical overall length of the pharingo-esophago-gastroscope amounts, for example, to 76 cm.

The invention can also be realized in a tracheo-bronchoscope for the examination of the trachea and the bronchial tubes. The advantages of the pharingo-esophago-gastroscope explained above also apply with such a tracheo-bronchoscope.

The endoscope of the invention is made up of a plurality of parts, namely of a fiberscope part, which includes, as a closed unit, the light/image transmission passage(s) and preferably one or more work passages, and of the one or more additional instruments. Since the additional instrument can, for instance, be set on the fiberscope part, this embodiment can also be termed a "pick-a-back system" (cf. FIG. 1). The additional instrument is here preferably located outside the actual fiberscope part.

The additional instrument can be set on the fiberscope part or, vice versa, the fiberscope part on the additional instrument in dependence on the cross-sectional area and shape of the body orifice, for example the meatus of the nose, and the additional instrument can have a smaller or larger cross-section than the fiberscope part.

The fiberscope part and the additional instrument(s) can be displaced relative to one another along their respective longitudinal directions (so-called "shuttle system"). In this way, a flexible handling and a variable radius of action of the relevant additional instrument result. For example, when biopsy forceps are used as the additional instrument, a displaceability of approximately 5 cm can be sufficient to, on the one hand, retract the biopsy forceps relative to the fiberscope part to avoid hindering the monitoring of the insertion procedure via the light/image transmission passage and to, on the other hand, extend the biopsy forceps relative to the stationary fiberscope part in a distal direction for the purpose of taking a sample.

A relative displaceability of approximately 35 cm can prove to be advantageous, in particular for long-term examinations where, with a stationary additional instrument, for example a pH measuring probe, only the fiberscope part should be displaced in order to carry out an optical monitoring at a certain pH measuring point without thereby disturbing or falsifying the continuing measurement with the pH measuring probe.

To achieve a connection of the fiberscope part and the additional instrument(s) to form a unit, a holding device is provided at the fiberscope part or at the relevant additional instrument. The fiberscope part and the additional instrument(s) can preferably be alternatively fixed to one another or released from one another by means of the holding device such that a relative movement between the fiberscope part and the additional instrument is possible.

For example, a loop—for example of nylon—can be provided as the holding device at the distal end of the endoscope relative to the operating physician and an additional instrument be held or guided therein. It is possible to allow the loop to project out of a central or a lateral opening at the distal end of the fiberscope part.

In particular, a work passage of, for example, 1 mm can be provided at the fiberscope part and fixation forceps of a diameter of, for example, 0.8 mm be guided therein, which engage at a closed loop of an overall length of approximately 60 mm. When this loop projects out of the work passage and engages around an additional instrument there, the relevant additional instrument can be fixed at the distal end of the fiberscope part or released for a relative movement respectively via the loop by a withdrawal or insertion of the fixation forceps.

As an alternative to this, it is possible to provide within a work passage of the fiberscope part a comparatively long loop which engages an additional instrument at the distal end of the endoscope and is operated, in particular tightened or released, by the physician at the proximal end of the endoscope (cf. FIGS. 5, 6a, 6b). The fixation forceps explained above can be dispensed with inside the work passage in this manner.

With appropriate use of the principles explained above, it is moreover possible to use a line guided through a work passage instead of a loop, the line being fixedly connected to the relevant additional instrument. It can be prevented in this way that the additional instrument unintentionally leaves the engagement by the loop when the loop is released.

In the embodiment of the endoscope of the invention with the fiberscope part and the additional instrument separated from one another, it is furthermore preferred if one or more fastening hoops are provided along the insertion section of the fiberscope part as holding devices in which one or more additional instruments are respectively guided by loose engagement.

Alternatively or additionally to the use of a loop, a jacket hose surrounding the fiberscope part completely or in part (cf. FIGS. 7a to 7c) or a side cover shaped or fastened laterally at the fiberscope part (cf. FIGS. 6a, 6b) can be provided for the reception of the additional instrument. The jacket hose or the side cover can be formed of plastic and/or elastically. Furthermore, the jacket hose or the side cover can be provided along the whole insertion section of the endoscope or along only one or more parts thereof.

In the event that the jacket hose or the side cover extends only along a part section of the endoscope, the jacket hose or the side cover can be formed displaceably with respect to the fiberscope part. It can thereby be ensured, for example in the use of the endoscope as a pharingo-esophago-gastroscope, that the jacket hose or the side cover is always arranged within the meatus of the nose and extending up to the pharyngeal cavity, and indeed irrespective of the penetration depth of the fiberscope part.

If, for example in the nasal insertion of the pharingo-esophago-gastroscope, the displaceable jacket hose is first arranged at the front end, that is, at the distal end of the fiberscope part, the jacket hose can maintain its position in the meatus of the nose from a certain penetration depth of the fiberscope part onwards, while the fiberscope part is inserted even further, for example for the observation of the esophagus. Even if the fiberscope part is subsequently retracted appropriately for the observation of the pharynx, the jacket hose maintains its position and is thus again arranged along the distal end of the fiberscope part. Only if the fiberscope part is completely pulled out of the meatus of the nose, is the jacket hose simultaneously taken along by the distal end of the fiberscope part.

The particular advantage of this embodiment lies in the fact that in each instance an additional instrument can be inserted without a problem and without pain along the fiberscope part, through the jacket hose and via the meatus of the nose into the pharyngeal cavity. The jacket hose namely prevents an injury to the meatus of the nose and to the pharyngeal cavity by the additional instrument, and the distal end of the additional instrument cannot unintentionally release from the fiberscope part due to the curvature to be overcome.

The explained displaceability of the jacket hose can be realized by the jacket hose being able to be displaced with respect to both the fiberscope part and the additional instrument and by covering the fiberscope part and optionally the additional instrument as a loose hose section. The side cover can, for example, be displaceably connected to the fiberscope part via a simple or a double rail-groove connection. Moreover, an abutment element, for example an annular broadening, can be provided at the proximal end of the jacket hose or the side cover in order to prevent a complete disappearance into the meatus of the nose. The endoscope can furthermore have a fixation device, for example a screw, via which the jacket hose or the side cover can be temporarily fixed with respect to the fiberscope part.

At least one groove and a rail corresponding thereto can furthermore be provided as the holding device to hold or guide the fiberscope part and the additional instrument and can respectively extend along the whole insertion section of the endoscope or along one or more parts thereof (cf. FIGS. 8, 9). One or more holding clamps can also be provided at the fiberscope part or at the additional instrument instead of the groove (cf. FIGS. 12, 13).

The holding device provided at the fiberscope part and the additional instrument can also be formed by one or more permanent magnets, for example made of an iron or nickel alloy, which cooperate with at least one counter-element made of a permanently magnetic or magnetic material, for example steel, aluminum or titanium.

In a particularly simple embodiment, this counter-element can be formed by the additional instrument or the fiberscope part itself. It is moreover possible to provide the permanent magnets or the counter-elements at a plurality of sections of the fiberscope part or of the additional instrument. The permanent magnet, the counter-element or both can have a covering of plastic to avoid a direct contact of the magnetic materials used and to reduce both the static friction and the sliding friction prevailing between the additional instrument and the fiberscope part.

Furthermore, a catch element and a hook element can be provided as the holding element at the fiberscope part, on the one hand, and at the additional instrument, on the other hand, or vice versa. It is possible in this way to insert, in particular to pull along, the hooked additional instrument into the body orifice by means of the fiberscope part. The additional instrument can subsequently be released in order to carry out movements and examinations independent of the position of the fiberscope part.

The catch element and the hook element are preferably each arranged at the distal end of the fiberscope part or the additional instrument respectively. The hook device can be formed, for example, by a laterally projecting undercutting lug and the catch element by a laterally projecting button lug engaging as required into the undercutting lug. If the catch element and the hook device are formed in a manner flattening towards the proximal end of the endoscope, the pulling of the fiberscope part or of the additional instrument out of the body orifice can take place particularly easily and safely.

It is naturally also possible to combine a plurality of the holding devices at one single endoscope.

The object underlying the invention is also satisfied for an endoscope of the kind initially mentioned by the unit of endoscope and additional instrument having a non-round cross-section along a longitudinal section (insertion section) to be inserted into a human or animal body orifice and by the light/image transmission passage or the plurality of light/image transmission passages and the additional instrument forming a closed unit (cf. FIG. 10).

A non-round cross-section of the insertion section, which is in particular matched to the cross-section of the body orifice or a meatus of the nose, is therefore also provided with this embodiment.

However, this endoscope forms, optionally together with one or more work passages, a closed unit so that when the endoscope is used for its intended purpose, the additional instrument is not separated from its own fiberscope part. This closed unit can be surrounded along its insertion section by a common jacket hose, for example of plastic, and it differs outwardly from a conventional gastroscope in particular by a non-round cross-section of the insertion section. The additional instrument can naturally also be formed displaceably with respect to the remaining endoscope in this embodiment (cf. FIG. 11a).

Each of the embodiments of the endoscope of the invention explained above can have at least one work passage into which an auxiliary means or an additional instrument can be inserted or which can serve for the carrying out of lavages or for the aspiration of bodily fluids.

The additional instrument named in connection with the invention can, but need not, form a part of the endoscope of the invention. Biopsy forceps, an aspirator/injector probe, a pH measuring probe, a manometric probe—for example for the examination of the esophagus peristole—, a Bilitec measuring probe for the measurement of the bilirubin content, a laser probe or other surgical instruments for therapeutic measures can be provided as the additional instrument. Moreover, a plurality of additional instruments, for example biopsy forceps and a pH measuring probe, can also be provided as a result of the optimized space utilization of the endoscope of the invention.

The known division into a light transmission passage on the one hand and an image transmission passage on the other hand can naturally be provided for the light/image transmission passage(s). For example, one or more light guides can form a light transmission passage. The image transmission passage can likewise be formed by light guides and associated optical systems or it can have an opto-electronic image converter at the distal end of the endoscope and corresponding electrical supply and transmission lines.

The endoscope of the invention can furthermore have one or more Bowden cable systems for the active lateral alignment. In this case, the swivel direction can coincide with the direction of the larger or the smaller cross-sectional dimension of the endoscope. With an endoscope to be inserted nasally, it is of advantage with respect to the change in direction required for the passage through the pharyngeal cavity if the endoscope can be actively swivelled at least in the direction of the larger cross-section dimension of the endoscope.

The endoscope of the invention, with its special advantages, can be used in many areas of endoscopy, for example in bronchoscopy. An advantageous application possibility also lies in the rinsing of body cavities, for example of the Eustachian tube or the maxillary sinus. The invention can furthermore be used in surgery, in particular for the carrying out of sterile work with the aid of additional instruments with simultaneous optical monitoring.

The invention is described below by way of example with reference to the drawings.

BRIEF DESCRIPTION OF THE DRAWINGS

FIGS. 1, 8, 10, 12, 14 and 16 are schematic side views respectively of an endoscope of the invention;

FIGS. 2, 6b, 9, 11a, 11b and 13 show in each case a section taken along the plane II—II of FIG. 1, the plane VI—VI of FIG. 6a, the plane IX—IX of FIG. 8, the plane XI—XI of FIG. 10, the plane XI—XI of FIG. 10 or along the plane XIII—XIII of FIG. 12;

FIGS. 3a and 3b are detailed views of the region III of FIG. 1;

FIGS. 15a, 15b, 15c and 15d are in each case a section taken along the plane XV—XV of FIG. 14 for different embodiments;

FIG. 17 is a detailed view of the region XVII of FIG. 16; and

FIG. 18 shows the lower side of the distal end of the additional instrument of FIG. 16 in a detailed view.

DESCRIPTION OF THE PREFERRED EMBODIMENTS

Figure 4:
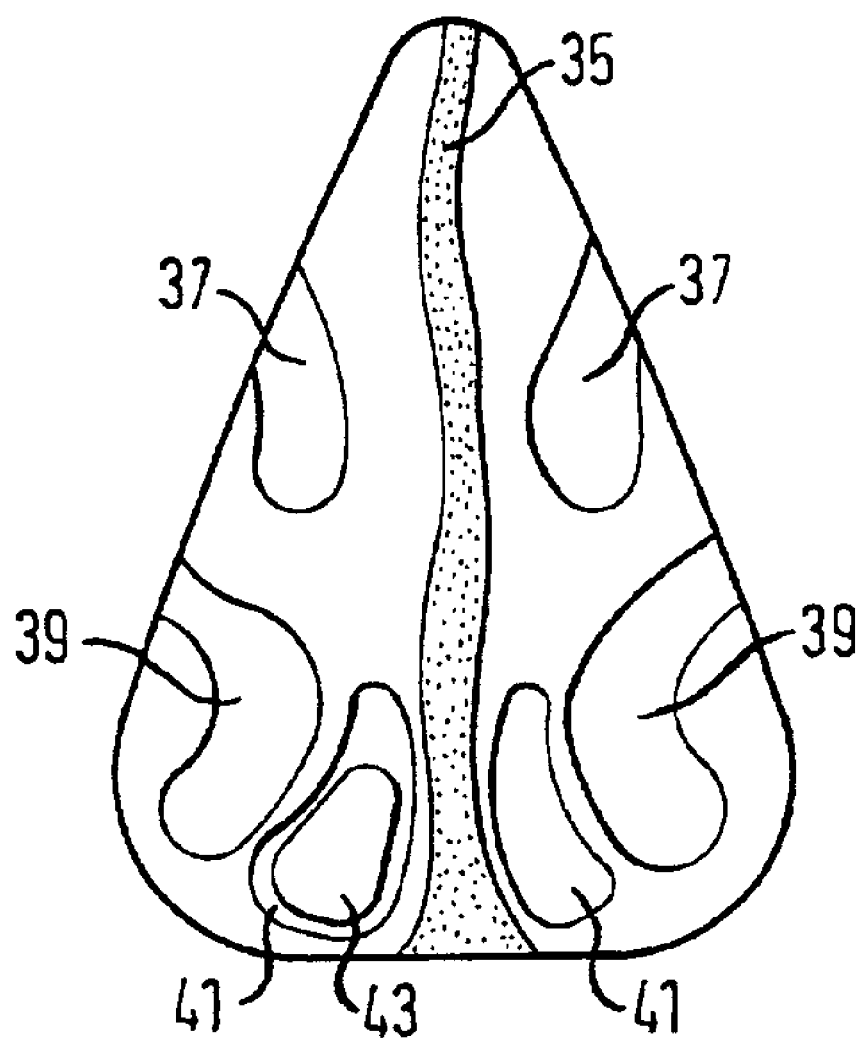
FIG. 4 is a schematic front section through a human nose.

FIG. 1 shows a side view of a pharingo-esophago-gastroscope of the invention. This has a fiberscope 11 with an elongate insertion section 13 and a proximal operating part 15. The open ends of two light transmission passages 17 and of an optical image transmission passage 19 as well as the ends—on the operator side—of fixation forceps 21 and a Bowden cable 23 are shown at the operating part 15, with their respective extents within the insertion section 13 of the fiberscope 11 not being shown in FIG. 1.

The endoscope of FIG. 1 further has an additional instrument 25 in the form of elongate biopsy forceps. This additional instrument 25 is connected to the fiberscope 11 at the distal end of the endoscope via a loop 27 and close to the operating part 15 by means of a fastening hoop 29.

FIG. 2 shows in a section through the insertion section 13 of the endoscope of FIG. 1 that the fiberscope 11 has a flexible jacket hose 31 as an outer cover and a central work passage 33 in which the fixation forceps 21 are guided. The Bowden cable 23 is not shown here.

FIGS. 3a and 3b each show detail views of the region III of FIG. 1, that is, of the distal end of the endoscope. The fixation forceps 21 guided in the work passage 33 hold the loop 27. This projects out of the fiberscope 11 and engages loosely around the biopsy forceps 25 to allow a relative movement of the fiberscope 11 and the biopsy forceps 25 (FIG. 3a). The loop 27 is pulled deeper into the work passage 33 by pulling back the fixation forceps 21 relative to the fiberscope 11 so that the free length of the loop 27 is reduced and the biopsy forceps 25 are fixed at the distal end of the fiberscope 11 (FIG. 3b). A different kind of loop holding can naturally also be provided instead of the fixation forceps 21.

The endoscope of FIGS. 1 to 3b formed by the fiberscope 11 and the additional instrument 25 can be inserted into the pharynx and subsequently into the esophagus and the stomach of a patient via a meatus of the nose. This manner of application is described in the following with reference to FIG. 4. This shows a frontal section of a nose having a nasal septum 35, two middle conchae 37 and two inferior conchae 39. The inferior nasal conchae 39 and the nasal septum 35 each bound an inferior meatus of the nose 41. An endoscope can be inserted into such an inferior meatus of the nose 41, preferably into the respectively larger one.

Due to the ultimately elongate cross-section of the meatuses of the nose 41, an endoscope of comparatively large cross-section 43 can be inserted if this cross-section—as shown in FIG. 4—does not have a circular shape, but a shape adapted to the relevant body orifice 41. In other words, more or larger additional instruments or light/image transmission passages can be inserted through the meatus of the nose with the endoscope formed in this manner than with a conventional fiberscope of round cross-section due to the improved utilization of area.

The overall cross-section of the endoscope of FIG. 1 is accordingly not circular, but—as visible from FIG. 2 for the unit of fiberscope 11 and additional instrument 25—modelled on the cross-section 43 shown in FIG. 4. The matched cross-section of the endoscope also gives this stability with respect to an unwanted rotation around its longitudinal axis. This is in particular of advantage with an active curvature and alignment of the endoscope by means of a Bowden cable.

If therefore the endoscope of FIG. 1 is inserted—as shown for the cross-section 43 in FIG. 4—via the meatus of the nose 41, then the flexible additional instrument 25 can be guided from the distal end of the fiberscope 11 via the loop 27, and indeed by a corresponding actuation of the Bowden cable 23. At the same time, the relevant body region can be illuminated in a known manner via the light transmission passages 17 and can be observed via the image transmission passage 19 and a corresponding optical system and video technique.

It must be noted with reference to the endoscope of FIG. 1 that while it is also possible to take a sample via the fixation forceps 21 guided in the central work passage 33, the work passage 33 of the fiberscope 11 typically has an inside diameter of only 1 mm. The fixation forceps 21 of accordingly less than 1 mm outside diameter can only take mucous tissue. In contrast, the biopsy forceps 25 of the endoscope of the invention can also take samples from deeper tissue layers due to its larger diameter.

Further embodiments of the endoscope of the invention are described in the following with reference to FIGS. 5 to 18, with same or similar elements as in FIGS. 1 to 3b each being characterized by the same reference numerals.

Figure 5:
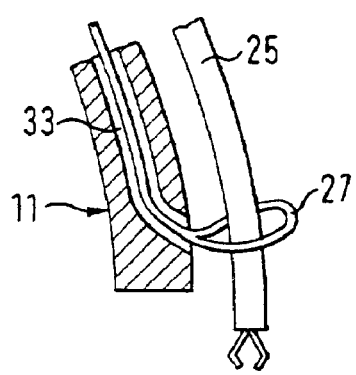
FIGS. 5 and 6a are detailed views corresponding to FIGS. 3a and 3b respectively of a further endoscope.

The embodiment of FIG. 5 differs from the endoscope of FIG. 1 in that the loop 27 is not held by a separate pair of fixation forceps 21, but is ultimately guided in one line through the work passage 33 up to an operating part (not shown). The work passage 33 does not open at the distal end face here, but at a side section of the distal end of the fiberscope 11.

Figure 6A:
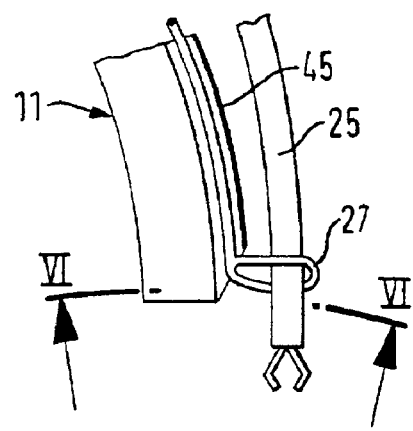

A single loop 27 without fixation forceps is also provided in the embodiment of FIG. 6a. The loop 27 is—in contrast to FIG. 5—not guided in a central work passage, but within a side cover 45 shaped at the fiberscope 11. This principle is also illustrated in the frontal sectional view of FIG. 6b. The chamfered opening of the side cover 45 at the distal end of the fiberscope 11 can be closed by an end piece (dummy) if the additional instrument 25 and thus the loop 27 are not required.

Figure 7A:
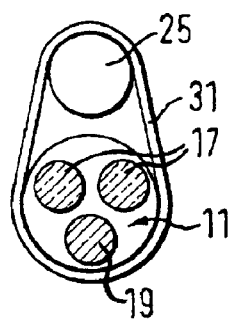
FIGS. 7a to 7c are sectional views corresponding to FIG. 2 of further endoscopes.

FIG. 7a shows a further endoscope of the invention in a cross-sectional view of its insertion section. A fiberscope 11 and an additional instrument 25 are also provided here as substantially separate components which are connected to one another via an elastic common jacket hose 31. As can be seen from FIG. 7b, this jacket hose 31 compresses on the removal of the additional instrument 25 in order to serve as an outer cover of only the fiberscope 11.

Figure 6B:
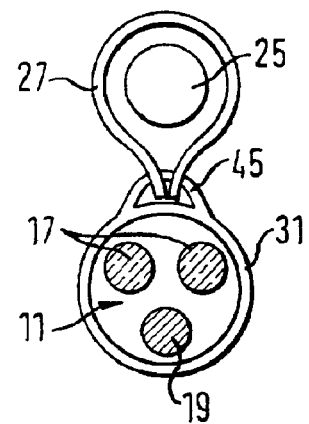
Figure 7B:
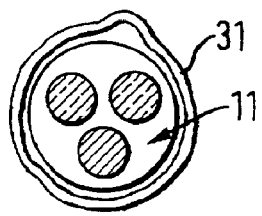
Figure 7C:
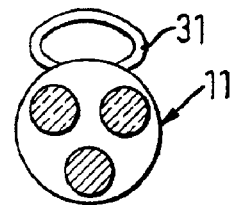

It is shown in FIG. 7c that the jacket hose 31—similar to the side cover 45 of FIGS. 6a and 6b—can also be provided only at one part of the periphery of the fiberscope 11 in order to optionally accept an additional instrument there.

Figure 8:
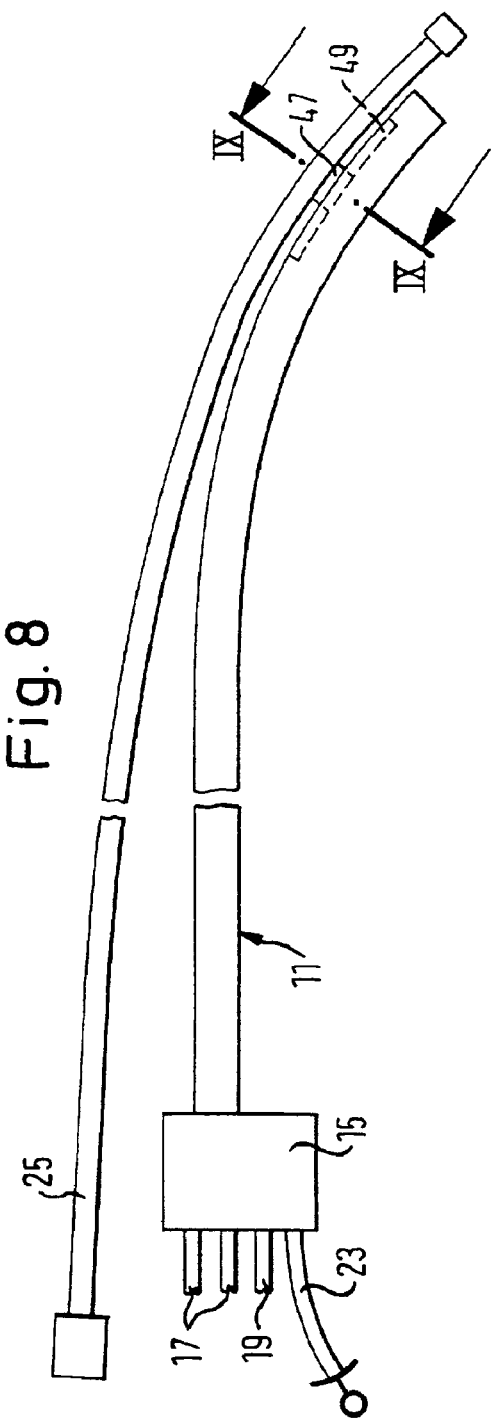
Figure 9:
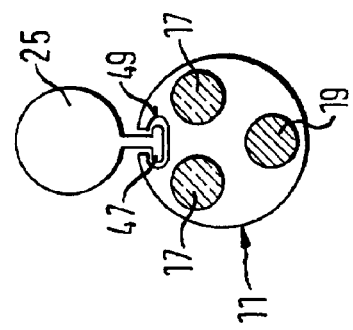

In the endoscope of FIG. 8, a fiberscope 11 and an additional instrument 25 are formed in the form of an aspirator/injector probe as units which are independent of one another and which are only connected to one another by a common holding device. As the sectional view of FIG. 9 shows, this holding device is formed by a guide lug in the form of a rail 47 formed at the additional instrument 25 and, on the fiberscope 11 side, by a corresponding groove 49. The groove 49 extends along the longitudinal direction of the fiberscope 11 by a much larger length than the length of the rail 47 so that a longitudinal displacement of the fiberscope 11 and the additional instrument 25 relative to one another is only possible within predetermined limits.

With this endoscope, a stabilizing device can be provided outside the body, in particular close to the operating part 15, for the additional stabilization of the fiberscope 11 and the additional instrument 25. This stabilization device can likewise be formed by a groove-rail system and can preferably be clipped to the fiberscope 11 and/or the additional instrument 25.

FIG. 10 furthermore shows an endoscope which, in contrast to the embodiments of FIGS. 1 to 9, is formed as a single closed unit and whose insertion section 13 has, in accordance with the invention, a non-circular cross-section. An additional instrument 25—for example biopsy forceps—is provided for this endoscope which can have a much larger cross-sectional diameter in comparison to additional instruments of corresponding conventional endoscopes. This is possible since the non-rotationally symmetrical cross-section of the endoscope allows a more flexible arrangement of the additional instrument 25, of the light/image transmission passages 17, 19 and of the Bowden cable 23 inside the insertion section 13, with the additional instrument 25 not necessarily being arranged at a central point.

The endoscope of FIG. 10 can, for example, have the cross-section shown in FIG. 11a. Here, a light transmission passage 17, an image transmission passage 19 and an additional instrument 25 guided inside a work passage 33 form a unit which is surrounded by a jacket hose 31 and which is similar to an isosceles triangle or a trapezium with rounded corners.

The cross-section of FIG. 11b likewise possible for the endoscope of FIG. 10 has a comparable, substantially triangular shape. The additional instrument 25 is here fixedly integrated in the endoscope, which can nevertheless—as visible in FIG. 10—be deformed and laterally aligned. In the special embodiment of FIG. 11b, two light transmission passages 17, an image transmission passage 19 and a separate rinsing passage 51 are furthermore provided.

FIG. 12 in turn shows an embodiment having an additional instrument 25 independent of the fiberscope part 11. The additional instrument 25 has—similar to the rail-groove connection of FIGS. 8 and 9—a plurality of holding clamps 53 which are distributed at equal intervals over its length and which each project laterally from the additional instrument 25 and engage around a rail 47 formed along the fiberscope part 11. As can be seen from the cross-sectional view of FIG. 13, the holding clamps 53 have a C-shaped cross-section and the rail 47 has a T-shaped cross-section.

A side cover 45, which facilitates the placing of the additional instrument 25 onto the rail 47 of the fiberscope part 11 and supports the insertion of the fiberscope part 11 with the fitted additional instrument 25 into the relevant body orifice, in particular the meatus of the nose, is formed on the fiberscope part 11 along a proximal section thereof. The additional instrument 25 fitted in this way can be moved as desired and without limitation along the fiberscope part 11. The additional instrument 25 can in particular be subsequently pushed in when the fiberscope part 11 is already inserted into the body orifice, with the fiberscope part 11 providing the required guidance.

In the endoscope of FIG. 14, biopsy forceps made of a magnetizable metal are provided as the additional instrument 25. As can be seen from the cross-sectional view of FIG. 15a, a permanent magnet 55 is integrated in the fiberscope part 11 which can magnetically attract the additional instrument 25. The additional instrument 25 is guided along the fiberscope part 11 due to this magnetic cooperation.

The additional instrument 25 is guided by a side cover 45 along a proximal part of the fiberscope part 11 for additional guidance and stabilization. The permanent magnet 55 is provided only section-wise along a distal part of the fiberscope part 11 such that an intentional release of the distal end of the additional instrument 25 from the fiberscope part 11 is possible at the relevant sections.

Since the jacket hose 31 surrounding the fiberscope part 11 and merging into the side cover 45 also serves as a covering 57 of the permanent magnet 55, the friction between the fiberscope part 11 and the additional instrument 25 is reduced and the relative movability increased.

FIG. 15b shows the cross-sectional view of a modified embodiment in which the side cover 45 is fastened to the jacket hose 31 via a double rail-groove connection and can thus be displaced along the whole fiberscope part 11. The side cover 45 can in this way always be left in the meatus of the nose 41 (FIG. 4) of the patient irrespective of the insertion depth of the fiberscope part 11 in order to facilitate the subsequent guiding of the additional instrument 25 without pain or injury. The rails of the side cover 45, which are T-shaped in cross-section, extend over the whole length of the side cover 45. The corresponding grooves at the fiberscope part 11 extend along the whole insertion section 13 up to just before the distal end of the fiberscope part 11.

FIG. 15c shows a further embodiment in which the side cover 45 is shaped at the jacket hose 31. In contrast to the embodiment of FIG. 15a, the unit of side cover 45 and jacket hose 31 is here pulled loosely over the fiberscope part 11 so that this unit can be displaced relative to both the fiberscope part 11 and the additional instrument. A stopper (not shown) at the distal end of the fiberscope part 11 can prevent an unintentional release from the fiberscope part 11.

FIG. 15d shows a further example corresponding to the embodiment of FIG. 15b of a rail-groove connection of a jacket hose 31 with a separate side cover 45 which is only provided along a part section of the fiberscope part 11 and can be displaced relatively thereto. In this example, a rail is provided on the fiberscope part 11 side, while a corresponding groove is arranged at the side cover 45. This reversed arrangement of rail and groove can reduce the risk of injury in some applications.

In the embodiment of FIG. 15d, the rail is moreover formed by the actual permanent magnet 55 rounded in cross-section. A volume reduction is thereby achieved within the fiberscope part 11 and the additional instrument 25 can contact the permanent magnet 55 directly at least outside the side cover 45 in favor of a higher magnetic attraction.

Finally, it is alternatively possible in the embodiment of FIG. 15d for the side cover 45 to engage around the only rail 55 in the manner of a clamp without a covering web 57 such that the additional instrument 25 can also lie directly on the rail 55 within the side cover 45.

FIGS. 16 and 17 show an endoscope having a manometric probe as the additional instrument 25. The distal end thereof is hooked to the distal end of the fiberscope part 11. A hook device 59 in the form of a laterally projecting undercutting lug is provided at the additional instrument 25 for this purpose and grips under, and partly around, a catch element 61 of the fiberscope part 11. The catch element 61 is formed by a button lug which projects laterally from the fiberscope part 11 and which is inserted along the longitudinal direction of the additional instrument 25 into an elongate slot 63 formed at the undercutting lug 59. The position of the hooked catch element 61 can be seen from FIG. 18, which shows the lower side of the additional instrument 25 in a detailed view.

The additional instrument 25 hooked in this way can be inserted into the body orifice jointly with the fiberscope part 11. If the additional instrument 25 is thereafter pushed beyond the fiberscope part 11, the catch element 61 leaves the hooking device 59. As a result, it is possible to work with the additional instrument 25 independently of the fiberscope part 11 and the additional instrument 24 can be removed from the body orifice again, in particular independent of the fiberscope part 11.

What is claimed is:

1. A deformable endoscope comprising a closed fiberscope part housing at least one light/image transmission passage and at least one work channel, at least one additional instrument, the fiberscope part being separable from the at least one additional instrument, a holding device including at least one permanent magnet associated with one of the fiberscope part and the at least one additional instrument and at least one counter-element made of magnetic material associated with the other one of the fiberscope part and the at least one additional instrument, the holding device holding and/or guiding the fiberscope part and the at least one additional instrument relative to one another, the fiberscope part and the at least one additional instrument forming a unit when not separated from each other which has a non-round cross-section along a longitudinal insertion section that is to be introduced into a body orifice, the permanent magnet and the at least one counter-element being displaceable relative to one another in a longitudinal direction of the unit for longitudinally displacing the fiberscope part and the at least one additional instrument relative to each other.

2. An endoscope in accordance with claim 1 wherein the additional instrument can be alternatively fixed at the fiberscope part by means of the holding device or released from the fiberscope part to allow relative movement in a longitudinal direction of the additional instrument and the fiberscope part.

3. An endoscope in accordance with claim 1 wherein one of a groove and a holding clamp and a corresponding rail or corresponding rail segments are provided as a holding device at the fiberscope part and at the additional instrument.

4. An endoscope in accordance with claim 1 wherein the counter-element is an integral part of one of the additional instrument and the fiberscope part; and/or wherein the permanent magnet is provided at a plurality of sections of the other one of the additional instrument and the fiberscope part.

5. An endoscope in accordance with claim 1 including one of a jacket hose and a side cover provided at the fiberscope part as a holding device for the acceptance of the additional instrument, the one of the jacket hose and the side cover extending along at least a part of the insertion section of the endoscope.

6. An endoscope in accordance with claim 1 wherein the jacket hose surrounds both the fiberscope part and the additional instrument.

7. An endoscope in accordance with claim 5 wherein the jacket hose is elastic with respect to its diameter.

8. An endoscope in accordance with claim 5 including a rail-groove connection which renders at least one of the jacket hose and the side cover displaceable relative to the fiberscope part.

9. An endoscope in accordance with claim 1 wherein a cross-section of the insertion section is matched to the body orifice.

10. An endoscope in accordance with claim 1 wherein a cross-section dimension of the insertion section is larger in one direction than in a direction orthogonal thereto.

11. An endoscope in accordance with claim 1 wherein the additional instrument comprises at least one of biopsy forceps, an aspirator/injector probe, a pH probe, a pressure measuring instrument and a Bilitec measuring probe.

12. An endoscope in accordance with claim 1 wherein the additional instrument is provided laterally spaced with respect to a center of the cross-section of the insertion section.

13. An endoscope in accordance with claim 10 including a Bowden cable for activating swiveling the endoscope in the direction of its larger cross-sectional dimension.

14. An endoscope in accordance with claim 9 wherein the endoscope comprises a pharingo-esophago-gastroscope for examining the pharynx, esophagus and/or stomach, and wherein a cross-section of the insertion section is matched to a cross-section of a meatus of a human nose.

15. An endoscope in accordance with claim 10 wherein the cross-section of the insertion section corresponds to one of an isosceles triangle and a mirror-symmetric trapezium, each including rounded corners and a base having a length of no more than approximately 3.5 mm.

16. An endoscope in accordance with claim 11 wherein a greatest cross-section dimension of the additional instrument is no more than about 3 mm.

17. An endoscope in accordance with claim 16 wherein the greatest cross-section dimension is no more than approximately 2 mm.

18. An endoscope in accordance with claim 1 wherein the fiberscope part and the additional instrument are displaceable relative to each other by up to approximately 35 cm in their longitudinal directions.

19. An endoscope according to claim 1 wherein the fiberscope part and the additional instrument are displaceable relative to each other by a length of up to approximately 5 cm.

20. An endoscope according to claim 1 wherein the light/image transmission passage comprises at least one separate light transmission passage and at least one separate image transmission passage.

21. An endoscope in accordance with claim 1 including a plastic covering for at least one of the permanent magnet and the counter-element.

22. A deformable endoscope comprising a closed fiberscope part housing a light/image transmission passage and a work channel, an additional instrument, the fiberscope part being separable from the additional instrument, a holding device including a permanent magnet and a counter-element made of magnetic material associated with the fiberscope part and the additional instrument, holding and/or guiding the fiberscope part and the additional instrument relative to one another, the fiberscope part and the additional instrument forming a unit when not separated from each other, the permanent magnet and the counter-element being displaceable relative to each other in a longitudinal direction of the unit for longitudinally displacing the fiberscope part and the additional instrument relative to each other.

* * * * *